United States Patent [19]
Misch et al.

[11] Patent Number: 6,045,361
[45] Date of Patent: Apr. 4, 2000

[54] BALL-TOPPED SCREW FOR FACILITATING THE MAKING OF AN IMPRESSION OF A DENTAL IMPLANT AND METHOD OF USING THE SAME

[75] Inventors: Carl E. Misch, Detroit, Mich.; J. Todd Strong, Birmingham, Ala.

[73] Assignee: Biohorizons Implant Systems, Inc., Birmingham, Ala.

[21] Appl. No.: 09/035,041

[22] Filed: Mar. 5, 1998

Related U.S. Application Data

[63] Continuation-in-part of application No. 08/829,764, Mar. 13, 1997, Pat. No. 5,927,979.
[60] Provisional application No. 60/037,194, Mar. 5, 1997.

[51] Int. Cl.[7] ................................................. A61C 9/00
[52] U.S. Cl. .................................... 433/214; 433/173
[58] Field of Search ............................. 433/213, 214, 433/173, 174, 175, 176, 172

[56] References Cited

U.S. PATENT DOCUMENTS

| | | | |
|---|---|---|---|
| 4,571,185 | 2/1986 | Rota | 433/173 |
| 4,793,808 | 12/1988 | Kirsch | 433/173 |
| 4,932,868 | 6/1990 | Linkow et al. | 433/174 |
| 4,955,811 | 9/1990 | Lazzara | 433/173 |
| 5,106,300 | 4/1992 | Voitik | 433/173 |
| 5,125,841 | 6/1992 | Carlsson et al. | 433/213 |
| 5,194,000 | 3/1993 | Dury | 433/173 |
| 5,213,502 | 5/1993 | Daftary | 433/172 |
| 5,334,024 | 8/1994 | Niznick | 433/173 |
| 5,338,196 | 8/1994 | Beaty et al. | 433/172 |
| 5,419,702 | 5/1995 | Beaty et al. | 433/214 |
| 5,476,383 | 12/1995 | Beaty et al. | 433/214 |
| 5,538,426 | 7/1996 | Harding et al. | 433/172 |
| 5,597,306 | 1/1997 | Horlitz et al. | 433/174 X |
| 5,662,475 | 9/1997 | Mena | 433/172 |
| 5,662,476 | 9/1997 | Ingber et al. | 433/213 |
| 5,674,071 | 10/1997 | Beaty et al. | 433/172 |
| 5,674,073 | 10/1997 | Ingber et al. | 433/213 |
| 5,681,167 | 10/1997 | Lazarof | 433/174 |

*Primary Examiner*—Nicholas D. Lucchesi
*Attorney, Agent, or Firm*—Needle & Rosenberg, P.C.

[57] ABSTRACT

A ball-topped screw for securing an abutment-mount to a dental implant while taking an impression of the abutment-mount using the indirect transfer method includes an elongated member having a first end and an opposite second end. A portion of the elongated member includes a threaded section for securing the first end of the elongated member and an abutment mount to a dental implant. A spherical member is affixed to the second end, whereby the spherical member provides a gripping shape for a dental impression material that has set around the spherical member while the elongated member secures an abutment mount to a dental implant.

1 Claim, 5 Drawing Sheets

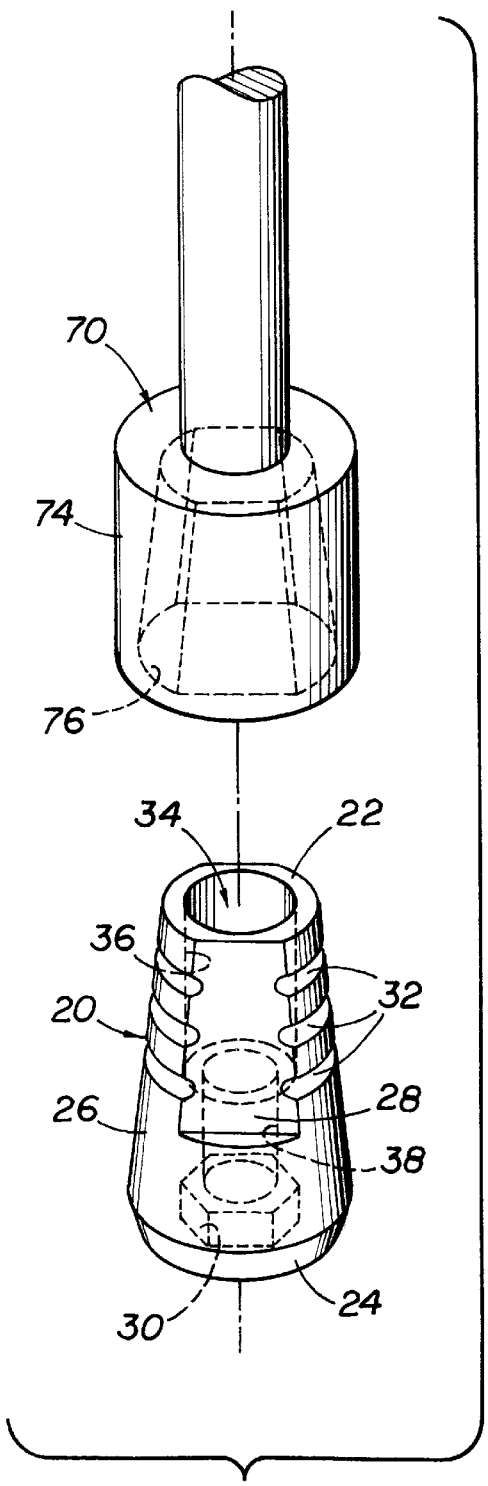
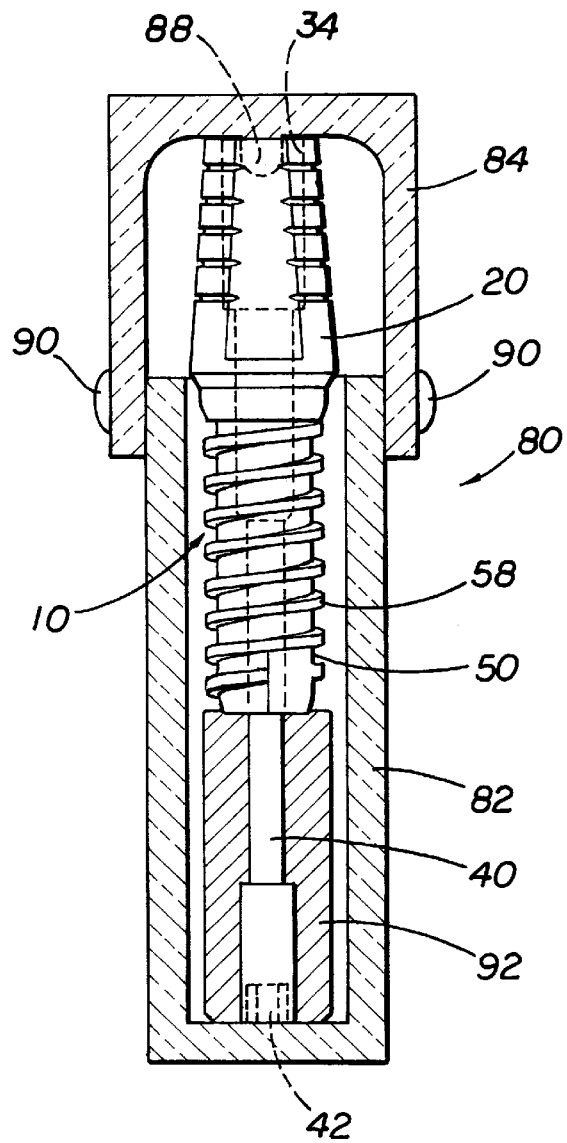
FIG 2
FIG 3

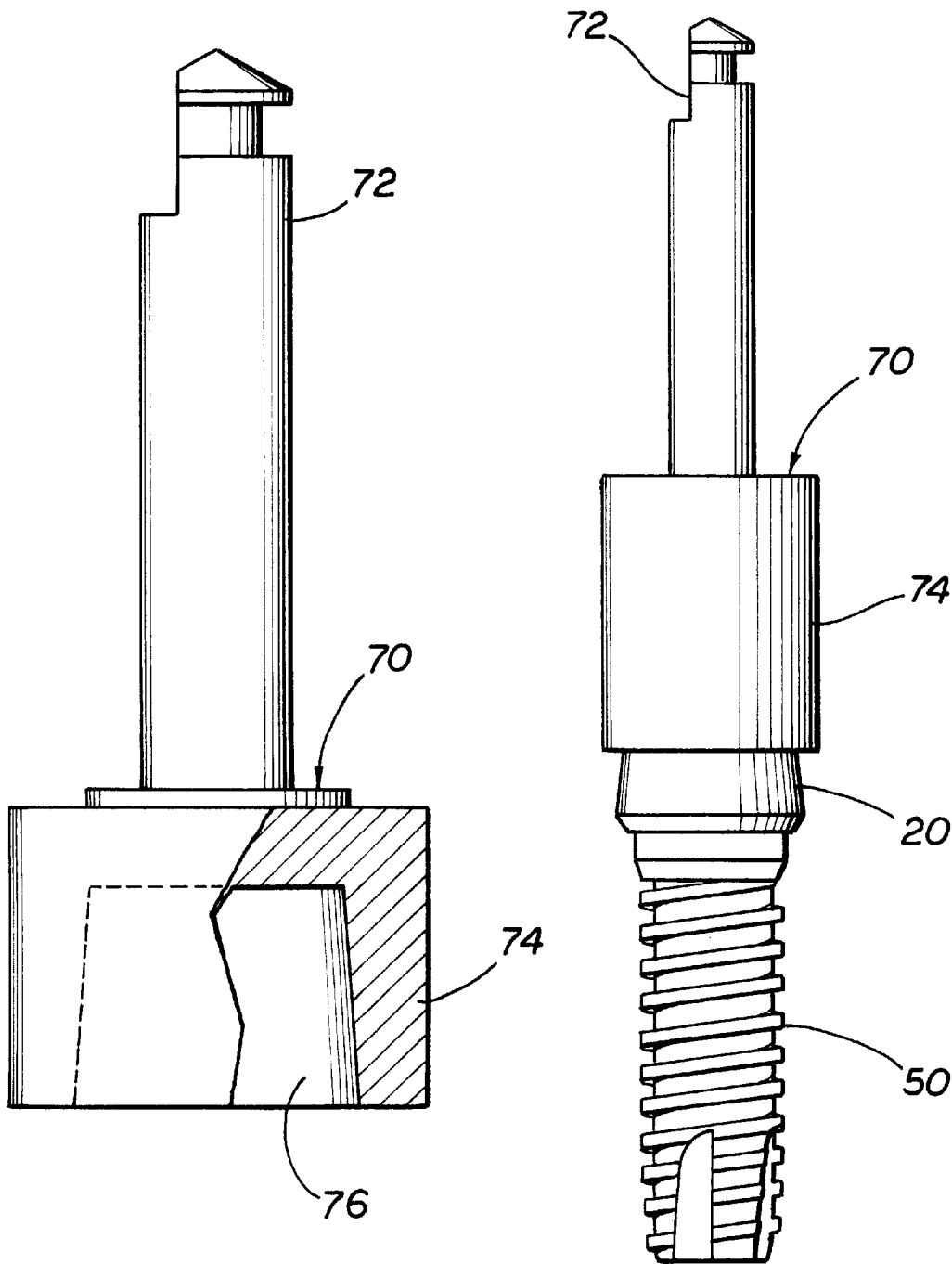
*FIG 4A*  *FIG 4B*

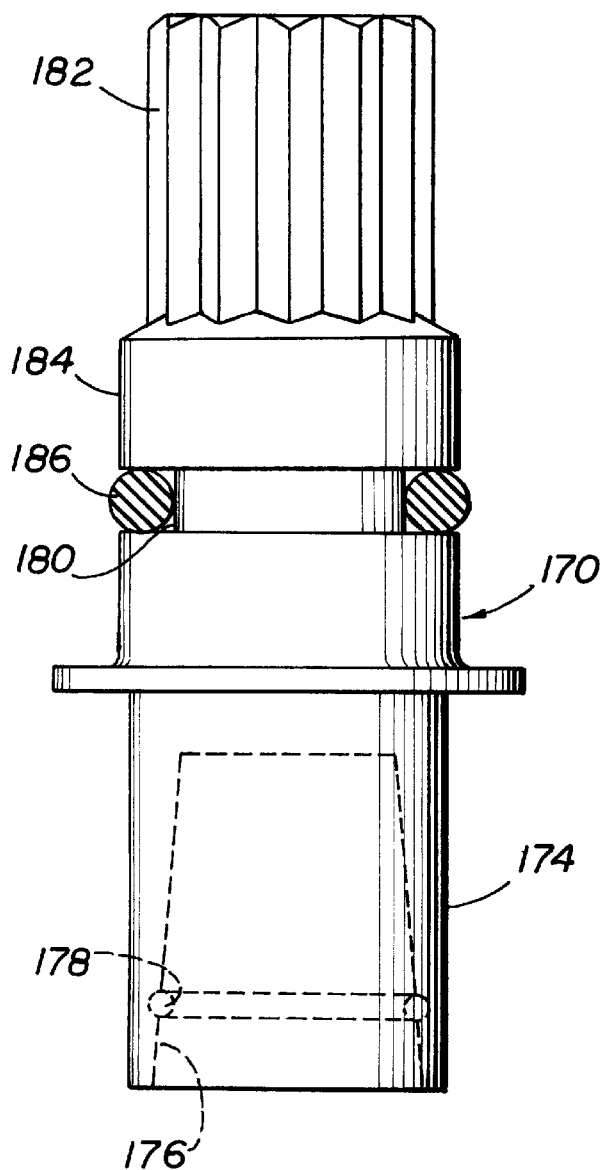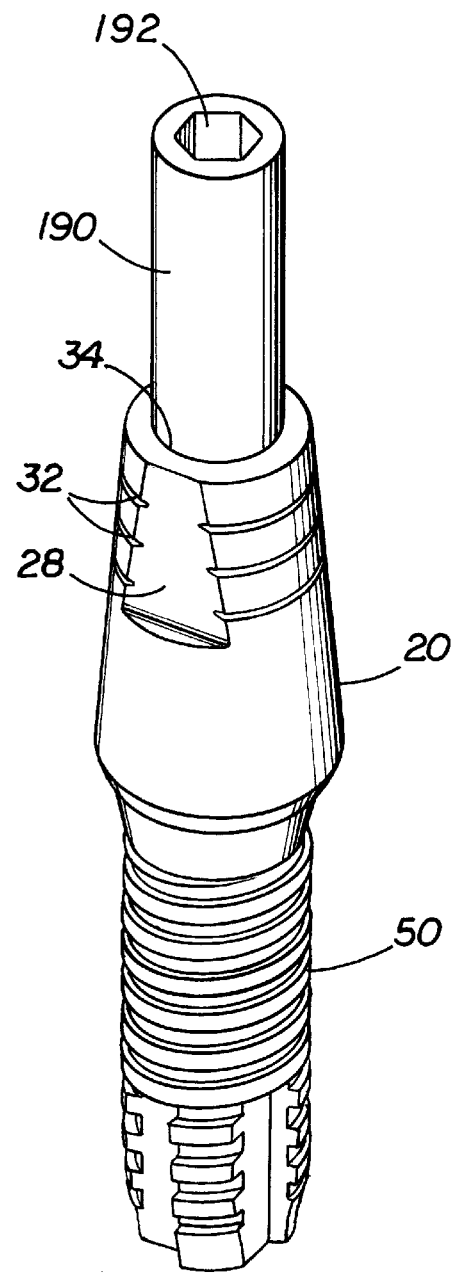
FIG 5  FIG 6

6,045,361

BALL-TOPPED SCREW FOR FACILITATING THE MAKING OF AN IMPRESSION OF A DENTAL IMPLANT AND METHOD OF USING THE SAME

CROSS-REFERENCE TO A PROVISIONAL APPLICATION

This application for letters patent claims priority under 35 U.S.C. § 119(e) on a provisional patent application, Serial No. 60/037,194, filed on Mar. 5, 1997.

CROSS-REFERENCE TO A RELATED APPLICATION

This is a continuation-in-part of our application Ser. No. 08/829,764 filed Mar. 31, 1997, now U.S. Pat. No. 5,927,979, the disclosure for which is incorporated herein by reference.

BACKGROUND OF THE INVENTION

1. Field of the Invention

The present invention relates to skeletal implants (such as dental implants) and more particularly to a coping screw used in making impressions of the area surrounding a dental implant, and a method for using the same.

2. Description of the Prior Art

Dental implants are used to provide a platform to which a dental prosthesis may be secured to underlying bone in the mandible or maxilla of a dental patient. A typical root form dental implant system employs a dental implant that is placed in a prepared site in the underlying bone. A disposable mount is used to provide a connection to an insertion tool used to place the implant into the bone. If the implant is a threaded implant, the mount is typically a removable extension of the implant that provides a hex nut-type suface for engagement with a socket used for screwing the implant into the prepared site. Once the implant is engaged in the site, the mount is removed and discarded. A cover screw is affixed to the top of the implant and the bone surrounding the prepared site is allowed to grow into the implant for several months, thereby securing the implant to the bone.

Once the surrounding bone has sufficiently engaged the implant, the cover screw is removed and an impression coping is affixed to the implant. An impression of the implant and the surrounding teeth is taken and a dental prosthesis is constructed using the impression as a model of the area of the patient's mouth surrounding the implant site.

One method of taking an impression is the "indirect" or "closed tray" method. With the indirect method, impression material is placed around the implant and allowed to set. Sometimes a "tray" is placed over the impression material before the impression material has set. Once it has set the tray an the impression material are removed from the patient's mouth, with the impression coping still affixed to the implant. The impression coping is removed from the implant and the gum surrounding the prepared site is allowed to heal. The impression is then used in making a model of the implant and the patient's mouth so that the prosthesis may be constructed. Although this method is convenient for the implantologist, it has the disadvantage of making it difficult for the prosthesis maker to precisely align the prosthesis with the implant and the abutment (a structure that extends from the implant to which the prosthesis is secured) during the prosthesis-making process.

Once made, the dental prosthesis is affixed to the abutment with cement, or other affixing means. Thus, the abutment acts as a platform for securing a dental prosthesis to the implant.

SUMMARY OF THE INVENTION

One aspect of the invention is a ball-topped screw for securing an abutment-mount to a dental implant while taking an impression of the abutment-mount using the indirect transfer method. The ball-topped screw includes an elongated member having a first end and an opposite second end. A portion of the elongated member includes a threaded section for securing the first end of the elongated member and an abutment mount to a dental implant. A spherical member is affixed to the second end, whereby the spherical member provides a gripping shape for a dental impression material that has set around the spherical member while the elongated member secures an abutment mount to a dental implant.

In another aspect, the invention is a method making a dental impression of an abutment mount affixed to a dental implant. A dental implant is placed in a selected site of a patient's bone in the patient's mouth. An abutment mount is placed on the dental implant. The abutment mount is fastened to the dental implant with a ball-topped screw. Dental impression material is applied to the patient's mouth in an area adjacent the abutment-mount so as to cover the abutment-mount and the ball-top screw. The impression material is removed from the patient's mouth after the impression material has set. The abutment-mount and the ball-top screw are removed from the implant and the abutment mount and the ball-top screw are replaced in the impression material.

These and other aspects of the invention will become apparent from the following description of the preferred embodiment taken in conjunction with the following drawings, although variations and modifications may be effected without departing from the spirit and scope of the novel concepts of the disclosure.

BRIEF DESCRIPTION OF THE FIGURES OF THE DRAWINGS

FIG. 2 is a top front perspective view of an abutment-mount and a socket.

FIG. 3 is a cross-sectional view of an implant kit packaged in a vial.

FIG. 4A is a partial cut-away elevational view of a first embodiment of a socket for use with a dental hand piece.

FIG. 4B is an elevational view of the socket of FIG. 4A engaged with an abutment-mount affixed to an implant.

FIG. 5 is a front elevational view of a second embodiment of a socket for use with a ratchet.

FIG. 6 is a top front perspective view of an implant and an abutment-mount using an elongated screw as part of a direct impression technique.

DETAILED DESCRIPTION OF THE PREFERRED EMBODIMENTS

Figure 1:
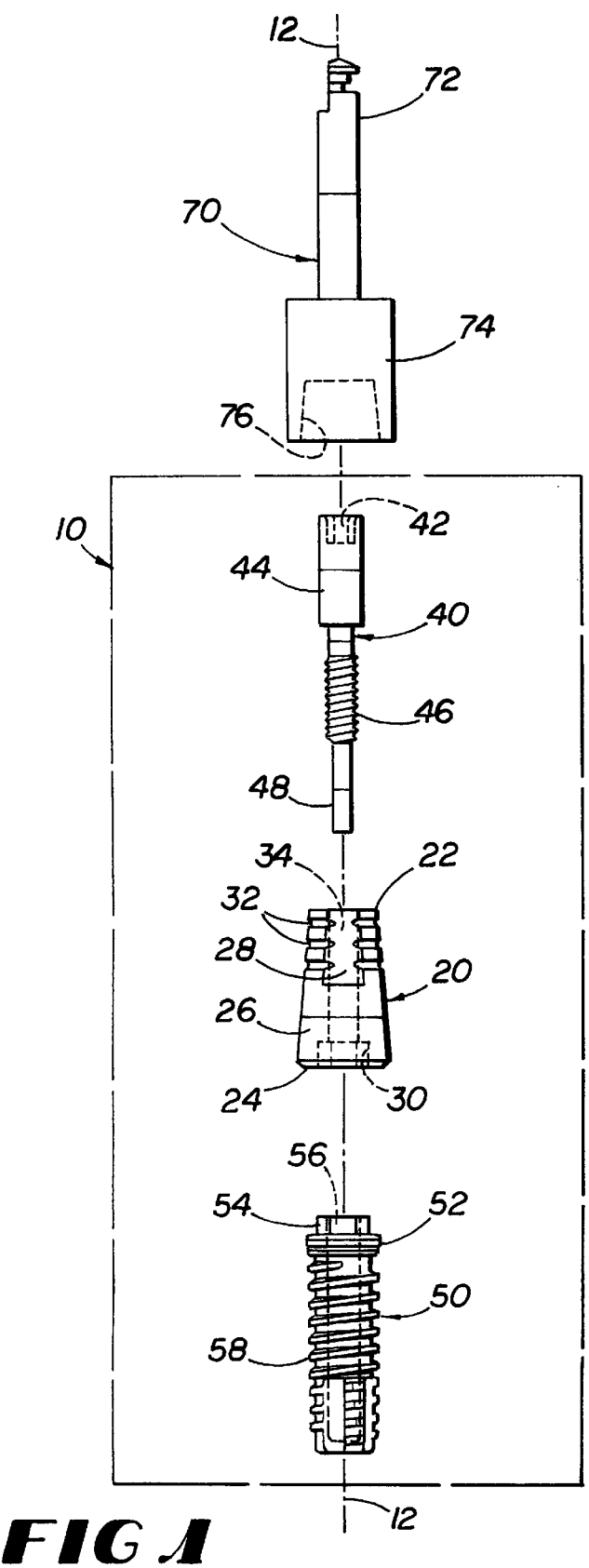
FIG. 1 is an exploded elevational view of an implant, an abutment-mount, an abutment screw and a socket for engaging the abutment-mount.

A preferred embodiment of the invention is now described in detail. Referring to the drawings, like numbers indicate like parts throughout the views. As used in the description herein and throughout the claims that follow, "a," "an," and "the" includes plural reference unless the context clearly dictates otherwise. Also, as used in the description herein and throughout the claims that follow, the meaning of "in" includes "in" and "on" unless the context clearly dictates otherwise. Also, "complimentary in shape" means generally having compatible dimensions, without necessarily having an identical shape.

As shown in FIGS. 1 and 2, the implant kit 10 of the present invention comprises a dental implant 50, an abutment-mount 20 and an abutment screw 40. The dental implant 50 may be one of several types, including the screw-type root-form dental implant shown. As show, the dental implant 50, the abutment-mount 20 and the abutment screw 40 are all aligned along a common axis 12. The implant 50, the abutment-mount 20 and abutment screw 40 would be made from a material suitable for implant applications, such as ASTM F-136 titanium alloy using a CNC machining process. As would be obvious to one skilled in the art, other materials and manufacturing processes may be employed without departing from the scope of the invention.

The abutment-mount 20 has a first end 22, an opposite second end 24 and a peripheral surface 26. At least one drive tool engagement surface 28 is provided for engagement with an implant drive tool 70, such as a socket. The engagement surface 28 could be a flat chordal surface, as shown, or any other of the many types of drive tool engagement surfaces that are commonly known to the arts of fastener design and implantology (for example, an internal hex could be employed for engagement with an Allen wrench as a drive tool).

The implant 50 includes a crestal end 52 and a first rotational engagement surface 54 adjacent the crestal end 52. The crestal end 52 defines a first longitudinal opening 56 with internal threads for receiving the abutment screw 40 therein. The abutment-mount 20 includes a second rotational engagement surface 30 that is complimentary in shape to the first rotational engagement surface 54. The first rotational engagement surface 54 may be a male polygonal surface (such as a hexagonal protrusion) extending from the crestal end 52, with the second rotational engagement surface 30 being a corresponding female engagement surface defined by the second end 24. Similarly, the first rotational engagement surface 54 could be a female polygonal surface, while the second rotational engagement surface 30 is a corresponding male polygonal surface. As would be obvious, many other types of engagement surfaces (including non-polygonal surfaces) could be employed with satisfactory results.

The abutment-mount 20 may be provided with one or more grooves 32 defined by the peripheral surface 26 to provide additional surface area on the abutment-mount 20 for cementing a dental prosthesis (not shown) thereto and for retention of impression material. Because the abutment-mount 20 performs both the function of an abutment, for securing a prosthesis to the implant 50, and the function of a mount, for driving the implant 50 into a prepared bone site, the present invention avoids the cost of supplying an additional, non-reusable mount.

The abutment-mount 20 is fastened to the implant 50 with the abutment screw 40. The abutment screw 40 may include a head portion 44, a threaded portion 46 and a non-threaded alignment portion 48 for aligning the threads of the threaded portion 46 with the threads in the first longitudinal opening 56 of the implant 50. The head portion 44 defines an internal hex opening 42 for receiving a hex driver for screwing the abutment screw 40 into the first longitudinal opening 56 of implant 50. The abutment-mount 20 defines a second longitudinal opening 34 passing therethrough, for receiving the abutment screw 40 therein. The second longitudinal opening 34 includes an enlarged top part 36 opening to the first end 22 and a narrowed part 38 opening to the second rotational engagement surface 30. The enlarged top part 36 has a diameter sufficient to receive the head portion 44 of the abutment screw 40, while the narrowed part 38 has a diameter sufficient to receive the threaded portion 46 of the abutment screw 40. The length of the enlarged part 36 is such that the head portion 44 is substantially flush with the first end 22 of the abutment-mount 20 when the abutment screw 40 and the abutment-mount 20 are properly affixed to the implant 50.

As shown in FIG. 3, the implant kit 10, including the implant 50, the abutment-mount 20 and cover screw 40 may be shipped together in a package 80 comprising a vial 82 and a cap 84. The vial 82 may be made of a plastic polymer, such as polyethylene, or any other suitable material commonly known to the art. At least one tab 90 extends outwardly from the cap 84 to prevent rolling of the package 80 when placed on a flat surface.

A detente 88 extends from the center of the inside surface of the cap 84. The detente 88 is shaped to fit into the second longitudinal opening 34 of the abutment-mount 20, so that the detentes 88 holds the kit 10 and prevents the threads 58 of the implant 50 from touching the inner surface of the vial 82. This is especially important, because the threads may be coated with a coating, such as an apatite compound, that could flake is touched by the vial 82. The abutment screw 40 is held in place by a plastic holder 92 that is polygonally-shaped (e.g. having a hexagonal shape) to prevent rolling of the holder and the abutment screw 40 when they are placed on a flat surface.

As shown in FIGS. 4A & 4B, in one embodiment designed for use with a standard dental handpiece (not shown), the drive tool 70 used to drive the implant 50 includes a socket 74 defining an opening 76 that is complimentary in shape to, and fits over, the abutment-mount 20. Extending upwardly from the socket 74 is a fitting 72 that couples to the dental handpiece. The fitting 72 shown herein is designed to be coupled to an ISO 1791-1 standard dental handpiece.

In an alternate embodiment, shown in FIG. 5, a drive tool 170 for use with a ratchet (not shown) may also be used. The drive tool 170 comprises a body portion 184, for engaging the ratchet, with a socket 174 extending downwardly therefrom and a finger knurl 182 extending upwardly therefrom. A recess 180 is defined by the body portion 184 for receiving therein an O-ring 186. The finger knurl 182 may be supplied to give the implantologist the ability to start the implant by hand. The socket 174 defines a recess 176 that is complimentary in shape to the abutment-mount. The recess 176 may be provided with an o-ring 178 that acts as a spacer to allow the abutment-mount to be easily disengaged from the socket 174.

As shown in FIG. 6, an elongated screw 190 may be supplied for use as an impression pin in the direct impression technique. The elongated screw 190 fits into the second longitudinal opening 34 of the abutment-mount 20 and has a drive structure 192, such as an internal hex, for tightening and loosening the elongated screw 190. In taking an impression using the elongated screw 190, impression material (not shown) is placed around the abutment-mount 20 and the elongated screw 190 after the implant 50 has been driven into the bone. The elongated screw 190 goes through the impression material and tray so that the drive structure 192 is not covered by the impression material. Once the impression material has set, the elongated screw 190 is removed from the implant 50 and the impression material and the emplaced abutment-mount 20 is removed from the patient's mouth. The grooves 32 on the abutment-mount 20 provide a surface which improves holding by the impression material. A healing screw (not shown) is affixed to the implant 50.

While the bone is affixing the implant, a cast of the area around the implant 50 is made from the impression material. The abutment-mount 20 may fit into the cast, thereby allowing a dental prosthesis to be constructed with the abutment-mount 20 providing a base with the same relationship to the patient's mouth as it will eventually have when it is permanently affixed to the implant 50. The drive tool engagement surface 28 provides a means of ensuring that the orientation of the abutment-mount 20 remains the same with respect to the implant 50 at all times. This function could also be accomplished by machining a marking onto the abutment-mount 20 to be used as a reference point. This ensures a near exact fit between the prosthesis, the abutment-mount 20 and the patients surrounding teeth.

Figure 7:
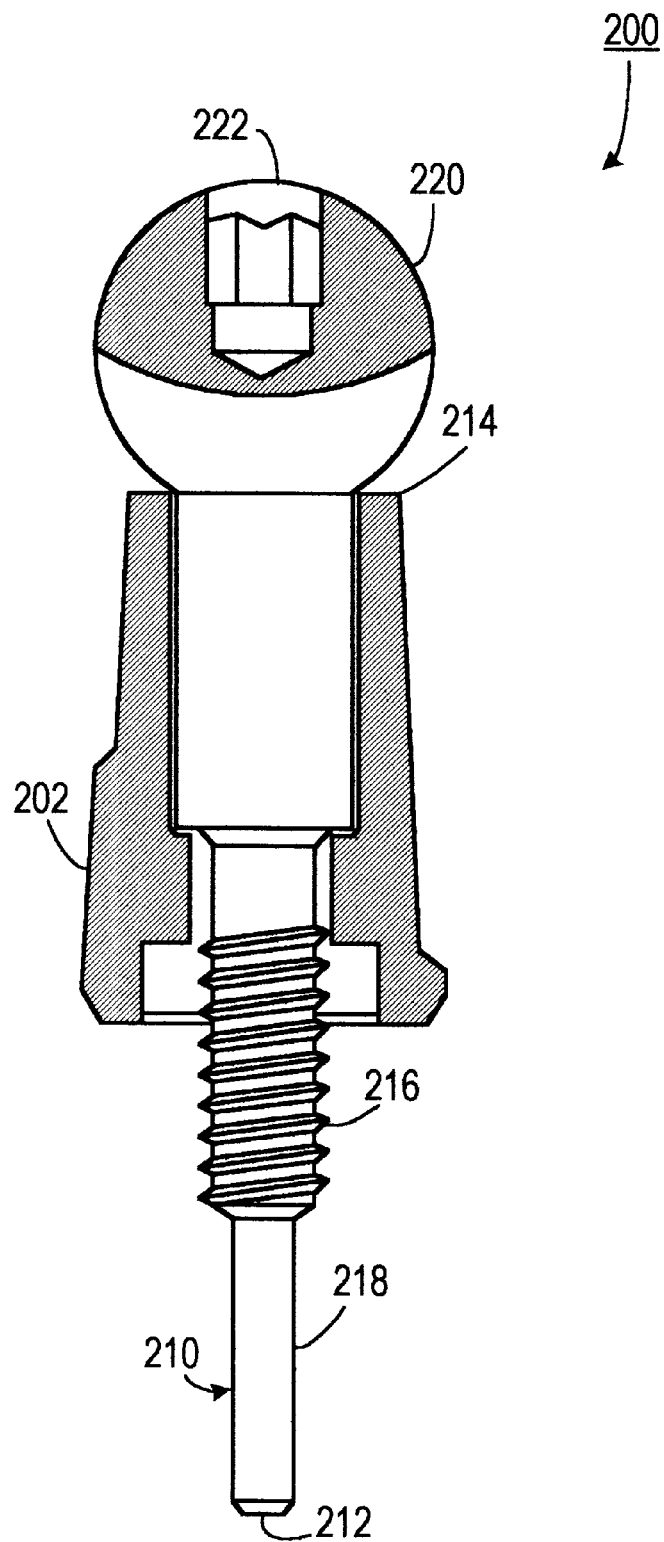
FIG. 7 is a cross-sectional view of a ball-top screw used to secure the abutment mount to the implant while taking a dental impression using the indirect transfer technique.

As shown in FIG. 7, one embodiment of the invention is a ball-topped coping screw 200, which includes an elongated member 210 having a first end 212 and an opposite second end 214. The elongated member 210 includes a threaded portion 216 for securing an abutment-mount 202 to a dental implant while taking a dental impression using the indirect transfer technique. Standard dental impression techniques may be employed in the making of the dental impression.

Affixed to the second end 214 is a spherical member 220 that provides a gripping shape for a dental impression material that has set around the spherical member 220 while the elongated member 210 secures an abutment mount 202 to a dental implant. The second end 212 may terminate in a non-threaded portion 218 that acts as a guide pin to prevent cross-threading of the threaded portion and the inside threaded surface of the implant.

In one embodiment, the spherical member 220 defines a cavity 222 having an inside polygonal surface to facilitate the driving of the elongated member 210 into a dental implant. The polygonal surface may be a hexagonal shape that is complimentary to a driving tool (not shown) for driving the ball-topped screw 200 into an implant (such as item 50 in FIGS. 1 and 2).

Closed tray techniques are often used in conjunction with one-piece, non-hexed transfer copings. These one-piece copings do not transfer the hex position of the implant because they are non-hexed. They are only used to provide a thread-timed transfer as well as emergence profiles of the implant (item 50 in FIGS. 1 and 2). By using the ball-topped screw 200 with the abutment-mount 202 (which is hexed and coupled to the external hex of the implant), the hex position of the implant is transferred to the master model as well as the emergence profile of the implant. The dentist also has an impression coping that is the actual abutment that will be used as the final restorative means (for cemented cases). Although the ball-topped screw 200 facilitates a hexed-timed transfer, the hex-timed transfer is only indicated for single tooth cases where hexed engagement between the implant and abutment is necessary to prevent rotation of the abutment during use. However, the indirect transfer coping "unit" still relates implant positional information to the master model that is critical for multi-unit restorations.

The ball-topped screw 200 can also be used to take an impression at the time of surgery. The surgeon removes the abutment screw that is used to attach the abutment-mount to the implant. The ball-topped screw 200 is then put in its place and an indirect transfer is taken. By taking an impression at the time of surgery, the dentist can begin critical lab work and reduce the number of visits required by the patient.

The indirect transfer technique, or closed tray, is quicker and easier than an open tray technique (also known as a direct transfer technique). The open tray method often requires a custom tray and is more technique sensitive; however the open tray technique is typically more accurate. A highly accurate impression is required for screw retained restorations but is not as important for cement retained restorations. Therefore, the closed tray technique using the indirect transfer coping unit is suitable for cement retained restorations. When used in conjunction with the abutment-mount, which is included in the implant package, the ball-topped screw 200 forms an indirect transfer coping unit. The indirect transfer coping unit allows the doctor to have an impression coping that will be used as the final abutment flexed timed transfer within a closed tray impression. (Currently, only an open-tray technique relates the hexed time transfer). The impression can easily be taken at the time of surgery by using the ball-topped screw 200 with the abutment-mount, which is already on the implant.

The above embodiments are given as illustrative examples and are not intended to impose any limitations on the invention. It will be readily appreciated that many deviations may be made from the specific embodiments disclosed in this specification without departing from the invention. Accordingly it is intended to cover all such modifications as within the scope of this invention.

What is claimed is:

1. A method making a dental impression of an abutment mount affixed to a dental implant, comprising the steps of:
 a. placing a dental implant in a selected site of a patient's bone in the patient's mouth;
 b. placing an abutment mount on the dental implant;
 c. fastening the abutment mount to the dental implant with a ball-topped screw;
 d. applying dental impression material to the patient's mouth in an area adjacent the abutment-mount so as to cover the abutment-mount and the ball-topped screw;
 e. removing the impression material from the patient's mouth after the impression material has set; and
 f. removing the abutment-mount and the ball-topped screw from the implant and replacing the abutment mount and the ball-topped screw in the impression material.

* * * * *